United States Patent
Reed (10) Patent No.: US 11,345,758 B2
(45) Date of Patent: May 31, 2022

(54) INHIBITION OF VASCULAR MATRIX METALLOPROTEINASE-9 TO TREAT ISCHEMIC INJURY

(71) Applicant: Translational Sciences, Inc., Paradise Valley, AZ (US)

(72) Inventor: Guy L. Reed, Paradise Valley, AZ (US)

(73) Assignee: Translational Sciences, Inc., Paradise Valley, AZ (US)

(*) Notice: Subject to any disclaimer, the term of this patent is extended or adjusted under 35 U.S.C. 154(b) by 0 days.

(21) Appl. No.: 16/626,071

(22) PCT Filed: Jun. 27, 2018

(86) PCT No.: PCT/US2018/039730
§ 371 (c)(1),
(2) Date: Dec. 23, 2019

(87) PCT Pub. No.: WO2019/005948
PCT Pub. Date: Jan. 3, 2019

(65) Prior Publication Data
US 2020/0207871 A1 Jul. 2, 2020

Related U.S. Application Data (60) Provisional application No. 62/525,505, filed on Jun. 27, 2017.

(51) Int. Cl.
| | | |
|---|---|---|
| A61K 39/395 | (2006.01) | |
| A61P 9/10 | (2006.01) | |
| C07K 16/40 | (2006.01) | |
| A61K 9/00 | (2006.01) | |
| A61K 38/49 | (2006.01) | |
| C12N 9/64 | (2006.01) | |
| A61K 39/00 | (2006.01) | |

(52) U.S. Cl.
CPC ............ *C07K 16/40* (2013.01); *A61K 9/0019* (2013.01); *A61K 38/49* (2013.01); *A61K 39/3955* (2013.01); *A61P 9/10* (2018.01); *A61K 2039/505* (2013.01); *A61K 2039/545* (2013.01); *C07K 2317/54* (2013.01); *C07K 2317/55* (2013.01); *C07K 2317/622* (2013.01); *C07K 2317/76* (2013.01); *C12N 9/6489* (2013.01); *C12Y 304/24035* (2013.01)

(58) Field of Classification Search
CPC ....... C07K 16/40; A61K 39/3955; A61P 9/10; C12N 9/6489; C12Y 304/24035
See application file for complete search history.

(56) References Cited

U.S. PATENT DOCUMENTS

| | | |
|---|---|---|
| 2003/0139332 A1 | 7/2003 | Noble et al. |
| 2007/0142337 A1 | 6/2007 | Schmid-Schonbein et al. |

FOREIGN PATENT DOCUMENTS

| | | |
|---|---|---|
| WO | 2010/048455 A1 | 4/2010 |
| WO | 2014/210062 A1 | 12/2014 |
| WO | 2015/127302 A1 | 8/2015 |
| WO | 2016/014808 A1 | 1/2016 |

OTHER PUBLICATIONS

Dorado et al, 2014. Current Cardiology Reviews. 10: 327-335.*
Martens et al (Biochimica et Biophysica Acta. 2007. 1770: 178-186).*
Ramos-DeSimone et al, 1993. Hybridoma. 12(4): 349-363.*
PCT International Search Report and Written Opinion for PCT Application No. PCT/US2018/039730 dated Sep. 18, 2018 (9 pages).
Amendment under PCT Article 34 and Reply to written Opinion of the ISA and Chapter II Demand for PCT/US2018/039730 submitted Apr. 29, 2019 (26 pages).
Fan et al., "Effects of Minocycline Plus tPA Combination Therapy after Focal Embolic Stroke in Type 1 Diabetic Rat," Stroke, 2013, 44(3):745-752.
Murata et al., "Extension of the Thrombolytic Time Window with Minocycline in Experimental Stroke," Stroke, 2008, 39(12):3372-3377.
Switzer et al., "MMP-9 in an Exploratory Trial of Intravenous Minocycline for Acute Ischemic Stroke," Stroke, 2011, 42(9):2633-2635.
PCT Written Opinion of the International Preliminary Examining Authority for PCT Application No. PCT/US2018/039730 dated Dec. 27, 2019 (9 pages).
Sigma-Aldrich Product Information for Anti-Matrix Metalloproteinase-9, Catalog No. M9570, 2012, pp. 1-2.
Sigma-Aldrich/Millipore, Product Information, Catalog No. MAB13415/ Clone Name GE-213, 2011, pp. 1-2.
Magid et al., "Expression of Matrix Metalloproteinase-9 in Endothelial Cells is Differentially Regulated by Shear Stress," The Journal of Biological Chemistry, 2003, 278(35):32994-32999.
Romanic et al., "Matrx-Metalloproteinase Expression Increases After Cerebral Focal Ischemia in Rats, Inhibition of Matrix Metalloproteinase-9 Reduces Infarct Size" Stroke, 1998, 29:1020-1030.
Supplementary European Search Report for EP Application No. 18824953 dated Mar. 11, 2021 (10 pages).

* cited by examiner

*Primary Examiner* — Zachary C Howard
(74) *Attorney, Agent, or Firm* — Eversheds Sutherland (US) LLP (57) ABSTRACT

Methods and pharmaceutical compositions for treating ischemic injury are provided. The methods include administering a therapeutically effective amount of a vascular matrix metalloproteinase 9 (MMP-9) inhibitor that reduces ischemic injury in a subject.

14 Claims, 6 Drawing Sheets

INHIBITION OF VASCULAR MATRIX METALLOPROTEINASE-9 TO TREAT ISCHEMIC INJURY

CROSS REFERENCE TO RELATED APPLICATIONS

This application claims the priority benefit of PCT/US2018/039730 filed on Jun. 27, 2018, which claims priority benefit of U.S. Provisional Patent Application No. 62/525,505 filed on Jun. 27, 2017, the entire contents of which are hereby incorporated herein by reference.

BACKGROUND OF THE INVENTION

Matrix metalloproteinase-9 (MMP-9), also known as gelatinase B, is an enzyme that degrades molecular components of the extracellular matrix and activates chemokines and cytokines involved in tissue remodeling.[1] MMP-9 expression is enhanced after ischemia of the brain,[2] liver[3], limbs and heart.[2]

In the brain, MMP-9 expression and activity increase within three hours after cerebral ischemia and reperfusion, and expression is closely correlated with breakdown of the blood-brain barrier (BBB).[4] Pathologic studies of human stroke show that MMP-9 expression (including the active form) is enhanced in neutrophils in microvessels in the area of stroke where there is degradation of type IV collagen, breakdown of the blood-brain barrier, and extravasation of blood.[5] MMP-9 expression is also detected in neurons and astrocytes in the peri-infarct cortex.[6]

In the ischemic brain, MMP-9 may play a key role in apoptosis, neuronal damage, hemorrhage, and blood-brain barrier breakdown, which is associated with brain swelling and cerebral edema.[7] Global deletion of MMP-9 protects against degradation of the barrier protein zonae occludens-1 and reduces blood-brain barrier breakdown and brain injury following acute cerebral ischemia.[8] Small molecule, non-specific MMP inhibitors that cross the BBB are neuroprotective when given in the first 24 hours after ischemic stroke, but they are harmful if given 7 days post-stroke.[6] MMP-9 is significantly induced after an increase in tissue plasminogen activator (tPA), yet experiments suggest that it does not contribute to brain bleeding.[9-12] Thus, there is controversy as to the role of brain (neuronal, glial, astrocytic) or vascular (endothelial, neutrophil) MMP-9 in these processes.[5,9,13]

Thromboembolic ischemic stroke causes blood-brain barrier breakdown, fibrin deposition, swelling, hemorrhage, and ischemic cell death. Elevated levels of matrix metalloproteinase-9 (MMP-9) correlate positively with ischemic brain injury in human stroke and animal models. However, the effects of intravascular vs brain MMP-9 on stroke outcomes are poorly understood.

SUMMARY OF THE INVENTION

The present disclosure provides methods and compositions for treating ischemic injury and related conditions. In certain embodiments, the invention provides pharmaceutical compositions and method for treating tissue injury after the onset of ischemia comprising: determining a subject is in need of therapy to reduce ischemic injury; and administering to the subject a therapeutically effective amount of a vascular matrix metalloproteinase 9 (MMP-9) inhibitor. In certain embodiments, the invention provides that the subject is a human or other mammal.

In embodiments, the invention provides compositions and methods of treatment for tissue injury, including ischemia, comprising administering to a subject in need thereof a treatment effective amount of a pharmaceutical composition that selectively inhibits vascular MMP-9. The selective inhibition of vascular MMP-9, but not localized tissue MMP-9 (e.g. MMP-9 in the brain), is therapeutically beneficial as localized tissue MMP-9 can have reparative effects. The pharmaceutical compositions also include antibodies that specifically bind vascular MMP-9 and that do not cross the blood-brain barrier.

BRIEF DESCRIPTION OF THE DRAWINGS

FIGS. 3A-3B show that MMP-9i reduces brain infarction in a humanized model of ischemic stroke. Brain infarction (FIG. 3A) and swelling (FIG. 3B) were assessed in a humanized model in which MMP-9−/− mice were given human MMP-9 (33 ug/kg mouse) 45 minutes prior to stroke. This was followed by saline (100 ul) or an MMP-9i antibody that inhibits human MMP-9 (166 ug/kg) given 15 minutes after administering the MMP-9. Experiments were performed in a randomized fashion by an operator blinded to treatment. Swelling and infarction were measured 24 hours after MCA thromboembolism in a blinded fashion. Means±SE are shown. The number of animals is indicated. $*p<0.05$, by Student's t-test.

FIGS. 5A-5D show selection of high avidity, specific MAbs that inhibit MMP-9 catalytic activity in a dose-related fashion. FIG. 5B shows the inhibitory effects of various purified MAbs on MMP-9 gelatinase activity. Purified human neutrophil MMP-9 (1 nM, Abcam) was mixed with purified monoclonal antibodies to human MMP-9 (100 nM), DQ-gelatin (3.75 ug/ml, 50 ul; Invitrogen) in assay buffer (50 mM Tris HCL, pH 7.6, 150 mM NaCl, 5 mM CaCl2, 0.01% Tween 20) in 96 well black microtiter plates (Costar #3915). The cleavage of DQ-gelatin was monitored by the released fluorescence at 37 degrees C. (ex. 485, em 530 nm). The percent inhibition of MMP-9 activity was determined in duplicate by comparison to wells without monoclonal antibody. FIG. 5C shows saturation binding studies of the lead MMP-9i to human MMP-9. Saturation binding of MMP-9i was examined in duplicate in microtiter plate wells coated with human MMP-9 (●, 2 ug/ml), mouse MMP-9 (○, 2 ug/ml), or bovine serum albumin (■, 10 mg/ml). The wells are washed to remove unbound MMP-9 and then non-specific protein binding sites were blocked with 1% bovine serum albumin for 1 hr. After washing, purified MMP-9i antibody diluted in 1% BSA was added to the wells in concentrations from $10^{-8}$ to $10^{-11}$ molar for 1 hr. The wells were washed. Then goat-antimouse Fab peroxidase antibody (1:5000) is added for 1 hr. The wells are washed. (In experiments with humanized MMP-9i, goat-antihuman Fab peroxidases are used instead). Then TMB (peroxidase substrate) is added to the wells and the product formation is monitored continuously at A405. The A405 is plotted vs. concentration of MMP-9i and the data are analyzed with GraphPad Prism to determine the $K_d$. An experiment is considered successful if the data analysis shows a fit with an r>0.95. A representative example of a binding study is shown. FIG. 5D shows specific binding of MMP-9i to the full size (~95 kDa) and catalytic subunits (~35 kDa) of human MMP-9. Purified recombinant human MMP-9 (1 ug/lane) were subjected to 7.5% SDS-PAGE under reducing conditions. After electroblotting to PVDF membranes the blots were blocked with 3% BSA and then incubated with purified MMP-9i (1 ug/ml) overnight at 4 deg. C. The blots were washed with TBS-tween and then incubated with a fluorescent antimouse secondary antibody (1:5000, Li-Cor). After washing the blots were developed on a Li-Cor system. The relative migration of standards and the position of MMP-9 proteins are shown.

DETAILED DESCRIPTION

In certain embodiments, the invention provides pharmaceutical compositions and method for treating tissue injury before, during or after the onset of ischemia comprising: determining a subject will be or is in need of therapy to reduce ischemic injury; and administering to the subject a therapeutically effective amount of a vascular matrix metalloproteinase 9 (MMP-9) inhibitor. In certain embodiments, the invention provides that the subject is a human or other mammal.

In certain embodiments, the invention provides that the vascular MMP-9 inhibitor is a monoclonal antibody or fragment thereof that binds human MMP-9. In certain embodiments, the invention provides that the vascular MMP-9 inhibitor specifically binds a catalytic subunit of MMP-9. In certain embodiments, the invention provides that the vascular MMP-9 inhibitor binds additional matrix metalloproteinases other than MMP-9. In certain embodiments, the invention provides that the pharmaceutical composition selectively inhibits vascular MMP-9, but not localized tissue MMP-9 (e.g., MMP-9 in the brain). In certain embodiments, the invention provides a vascular MMP-9 inhibitor does not cross the blood-brain barrier. In certain embodiments, the invention provides that the vascular MMP-9 inhibitor is administered parenterally or intravascularly.

In certain embodiments, the invention provides that the vascular MMP-9 inhibitor is administered following thromboembolic stroke in the subject. In certain embodiments, the invention provides that the vascular MMP-9 inhibitor is administered at least fifteen minutes after thromboembolic stroke in the subject. In certain embodiments, the invention provides that the vascular MMP-9 inhibitor is administered at least thirty minutes after thromboembolic stroke in the subject.

In certain embodiments, the invention provides that the vascular MMP-9 inhibitor is administered before thromboembolic stroke in the subject. In certain embodiments, the invention provides that the patient is further treated with tissue plasminogen activator or other therapy before or after the administration of the MMP-9 inhibitor.

In certain embodiments, the invention provides that the subject is treated with a stentreiever or other type of thrombectomy device before or after the administration of MMP-9 inhibitor.

In certain embodiments, the invention provides that the vascular MMP-9 inhibitor decreases vascular MMP-9 activity in the subject. In certain embodiments, the invention provides that administration of the vascular MMP-9 inhibitor decreases organ infarction, ischemic cell death, organ swelling, organ hemorrhage, blood barrier breakdown, fibrin deposition, or a combination thereof. In certain embodiments, the invention provides that administration of the vascular MMP-9 inhibitor decreases cerebral infarction, ischemic cell death, brain swelling, brain hemorrhage, blood-brain barrier breakdown, fibrin deposition, or a combination thereof. In certain embodiments, the invention provides that the subject has ischemic injury to a tissue selected from a brain, a liver, a limb, a heart, or a combination thereof.

In certain embodiments, the invention provides a pharmaceutical composition for treatment according to any of the described methods, comprising: a therapeutically effective amount of a vascular matrix metalloproteinase 9 (MMP-9) inhibitor; and a pharmaceutically acceptable carrier.

In certain embodiments, the invention provides a method of treating tissue injury comprising administering to a patient in need thereof a treatment effective amount of MMP-9 inhibitor and a plasminogen activator. In embodiments, the administration can be a co-administration of a unitary pharmaceutical composition, or administration of separate pharmaceutical compositions in either order. In embodiments, the invention provides a kit comprising a MMP-9 inhibitor and a plasminogen activator, and instructions for administration for treating tissue injury after the onset of ischemia. In embodiments, the MMP-9 inhibitor is a monoclonal antibody or fragment thereof that binds human MMP-9, and the plasminogen activator is tissue plasminogen activator (tPA). Monoclonal antibodies that bind to MMP-9, such as human MMP-9, are commercially available, such as from EMD Millipore, ThermoFisher, or Sigma Aldrich (GE-213, MAB13415) and can also be made by methods well-known to those skilled in the art.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "antibody" refers to an intact immunoglobulin (Ig) molecule of any isotype, or an immunologically active fragment thereof that can compete with the intact antibody for specific binding to the target antigen, e.g., MMP-9. MMP-9 antibodies are commercially available and well-known, and can be routinely made given the well-known identity of MMP-9 for humans and other mammals. In some instances, the antibody is an immunological fragment of an intact antibody (e.g., a $F_{ab}$, a $F_{ab'}$, a $F_{(ab')2}$, or a single-chain Fv fragment scFvs). Antibodies include, but are not limited to, monoclonal antibodies, polyclonal antibodies, bispecific antibodies, minibodies, domain antibodies, synthetic antibodies, chimeric antibodies, humanized antibodies, human antibodies, antibody fusions, and fragments thereof, respectively. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. The basic antibody structural unit typically comprises a tetramer. Each such tetramer typically is composed of two identical pairs of polypeptide chains, each pair having one full-length "light" (about 25 kDa) and one full-length "heavy" chain (50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. Certain classes such as IgG and IgM have subclasses as well (e.g. $IgG_1$, $IgG_2$, $IgG_3$, $IgG_4$, and so forth).

As used herein, "monoclonal antibody" or "MAb" refers to a population of antibodies that are made by identical immune cells that are all clones of a unique parent cell.

As used herein, "antigen binding region" refers the part of an antibody molecule that contains the amino acid residues that interact with an antigen and confer on the antibody molecule its specificity and affinity for the antigen. An antigen binding region typically includes one or more "complementary binding regions" ("CDRs"). A "CDR" is an amino acid sequence that contributes to antigen binding specificity and affinity. Certain antigen binding regions also include one or more "framework" regions. "Framework" regions can aid in maintaining the proper conformation of the CDRs to promote binding between the antigen binding region and an antigen. Structurally, framework regions can be located in antibodies between CDRs.

As used herein, "epitope" refers to a region of an antigen that is bound by an antibody that targets that antigen, and typically includes specific amino acids that directly contact the antibody. Generally, antibodies specific for a particular target antigen will preferentially recognize an epitope on the target antigen in a complex mixture of proteins and/or macromolecules.

As used herein, "immunological binding," refers to the non-covalent interactions of the type which occur between an antibody molecule and an antigen for which the antibody is specific. The strength, or affinity, of immunological binding interactions can be expressed in terms of a dissociation constant ($K_d$) of the interaction, wherein a smaller $K_d$ represents a greater affinity. Immunological binding properties of selected antibodies can be quantified using methods well known in the art. One such method entails measuring the rates of antigen-binding site/antigen complex formation and dissociation wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables the cancellation of all parameters not related to affinity, and is equal to the dissociation constant $K_d$. An antibody of the present disclosure is said to specifically bind its target antigen when the dissociation constant ($K_d$) is ≤1 µM. An antibody of the present disclosure specifically binds antigen with "high affinity" when the $K_d$ is ≤5 nM, and with "very high affinity" when the $K_d$ is ≤0.5 nM.

Variations in the amino acid sequences of antibodies are contemplated as being encompassed by the present disclosure, providing that the variations in the amino acid sequence maintain at least 75%, more preferably at least 80%, 90%, 95%, and most preferably 99%. Certain percentages in between are included, such as 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, and 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional antibody can readily be determined by assaying the specific activity of the antibody derivative. Fragments or analogs of antibodies can be readily prepared by those of ordinary skill in the art. Preferred amino- and carboxy-termini of fragments or analogs occur near boundaries of functional domains.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such antibodies. Antibodies can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

As used herein, "substantially pure" means an object species is the predominant species present (i.e., on a molar basis it is more abundant than any other individual species in the composition), and preferably a substantially purified fraction is a composition wherein the object species comprises at least about 50% (on a molar basis) of all macromolecular species present. Generally, a substantially pure composition will comprise more than about 80% of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As used herein, "patient" and "subject" are used interchangeably and include human and veterinary subjects.

As used herein, "target antigen" refers to a molecule or a portion of a molecule capable of being selectively bound by an antibody. In certain embodiments, a target can have one or more epitopes. In this context, it does not require that the molecule be foreign or that it be capable of inducing an immune response.

As used herein, "pharmaceutical composition" refers to a pharmaceutically acceptable composition containing chemical compound, composition, agent or drug capable of inducing a desired therapeutic effect when properly administered to a patient. It does not necessarily require more than one type of ingredient.

As used herein, "pharmaceutically acceptable carrier" refers to an excipient, diluent, preservative, solubilizer, emulsifier, adjuvant, and/or vehicle with which an active agent is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art.

As used herein, "therapeutically effective amount" refers to the amount of a therapeutic agent determined to produce a therapeutic response in a patient. Such therapeutically effective amounts are readily ascertained by one of ordinary skill in the art.

As used herein, "inhibitor" refers to a composition that decreases the magnitude of at least one activity or function of a molecule when compared to the magnitude of the activity or function observed in the absence of the inhibitor. Certain exemplary activities and functions of a molecule include, but are not limited to, binding affinity, enzymatic activity, and signal transduction.

As used herein, "treat" and "treatment" include therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors.

As used herein, "prevent" does not require the 100% elimination of the possibility of an event. Rather, it denotes that the likelihood of the occurrence of the event has been reduced in the presence of the compound or method.

EXAMPLES

Example 1

To study the effects of MMP-9 deficiency and MMP-9 supplementation on mice outcomes following thromboembolic stroke.
Methods Thromboembolic stroke was induced by injecting autologous clots into the proximal middle cerebral artery in some mice. To mimic ischemic stroke treated with reperfusion, stroke was also induced by occlusion of the middle cerebral artery by a filament in another set of mice. In both sets of mice, 24 hours after stroke initiation, swelling, hemorrhage and cerebral infarction were quantitated. MMP-9 expression, BBB breakdown, fibrin deposition (immunostaining) and cell death (TUNEL staining) were quantitatively determined. The data were analyzed by Student's t-test or one-way ANOVA.

Results

After 24 h stroke, MMP-9 expression was specifically upregulated in the ischemic hemisphere and co-localized with neutrophils and the endothelium. In comparison to MMP-9+/+ mice, MMP-9−/− mice showed a significant decrease in cerebral infarction (p<0.05), swelling (p<0.01) and a nonsignificant decrease in brain hemorrhage. BBB breakdown (p<0.05), fibrin deposition (p<0.01) and cell death (p<0.01) were also significantly decreased in MMP-9−/− mice. Intravenous MMP-9 supplementation (45 min before stroke) to MMP-9−/− mice reversed the beneficial effects of MMP-9 deficiency. Cerebral infarct and swelling were restored in MMP-9 supplemented MMP-9−/− mice to levels equivalent to MMP-9+/+ mice demonstrating the role of intravascular MMP-9 in ischemic stroke injury.

Conclusions

Intravascular MMP-9 has profound deleterious effects on BBB breakdown, swelling, hemorrhage and cell death in ischemic stroke. Targeted inhibition of vascular MMP-9 can prove beneficial for reducing ischemic brain injury.

Example 2

To test whether vascular MMP-9 contributes to acute ischemic brain injury in experimental thromboembolic stroke and whether selective inhibition of vascular MMP-9 may reduce blood-brain barrier breakdown and ischemic brain injury.

Methods

Experimental Ischemic Stroke. After randomization, adult C57Black/6J mice or congenic MMP-9$^{-/-}$ mice (~25-35 g, Jackson Labs, Bar Harbor, Me.) are anesthetized with isoflurane. Experiments are performed by a blinded investigator. Autologous thromboemboli are made with pooled fresh frozen mouse plasma as has been described.[14] Mice are ventilated with 1.5-2% isoflurane and $O_2$. Temperature is maintained at 37 degrees C. The left common carotid artery is isolated, and the external carotid, thyroid, and occipital arteries are ligated. Microvascular clips are placed temporarily on the common and internal carotid arteries. A PE8 catheter containing the clot is inserted through a small arteriotomy in the external carotid artery for retrograde passage through the internal carotid artery to the origin of the middle cerebral artery (MCA); the thrombus is embolized at a speed of 0.45 mL/min in a volume of 200 μl saline. A laser Doppler flow probe (described below)[15, 16] indicates appropriate embolization by a decline in hemispheric blood flow by ≥80%. Mice are treated in a randomized fashion with the operator blinded to treatment. MMP-9i or placebo, if given, are administered as a bolus. Two MMP-9i's were tested: affinity-purified goat anti-mouse MMP-9 (Sigma, M9570, Lot MKBV0351V) and anti-human MMP-9 (Sigma, GE-213, MAB13415). Euthanasia is performed at the indicated time or earlier if mice appeared moribund, in discomfort, etc. according to study criteria. After euthanasia, blood is collected by cardiac puncture and saline tissue perfusion is performed as described.[17] In another series of experiments, the effect of MMP-9i on reducing ischemic brain injury was examined in mice treated with recombinant tissue plasminogen activator (r-tPA) after filament arterial occlusion followed by reperfusion. Experiments were performed by an operator blinded to treatment. The middle cerebral artery was occluded by a filament in anesthetized, congenic C57Bl6 mice for 180 min. Then mice were treated with r-tPA (10 mgs/kg) with or without an antibody MMP-9i (5 ugs in 100 ul) intravenously, as indicated. The r-tPA was administered 10% as a bolus and 90% over 30 min. Infarction, swelling, and hemorrhage were measured 24 hours in a blinded fashion.

Cerebral Blood Flow. Cerebral blood flow in the MCA territory is monitored by a blood flow meter (ML-191, ADInstruments, Oxford Optonix, UK) using a laser Doppler probe (MSF 100XP, ADInstruments) through a fiberoptic filament attached by use of a tissue adhesive to the intact skull 2 mm caudal to bregma and 6 mm lateral to midline of the affected hemisphere.[16] Blood flow is recorded using a Power Lab 2/26 data acquisition system (ADInstruments) and successful MCA occlusion is confirmed by an ~80% drop in blood flow relative to baseline pre-embolism.

Analyses of Brain Hemorrhage, Infarction, and Swelling.

Immediately after the euthanasia and perfusion, the brains are isolated and sliced coronally into 2 mm sections in a rostral-caudal orientation. Both faces of the brain slices are immediately digitally photographed through a microscope. Brain slices are promptly incubated in triphenyl tetrazolium chloride (TTC, 2%) to assess cellular viability followed by digital photography as above. Digital microscopic images are analyzed by a blinded observer using Image Pro Plus 6.2 software to measure areas of brain hemorrhage, TTC staining and hemisphere swelling. To determine the percent hemisphere infarction, the TTC-stained areas of the ischemic and non-ischemic hemispheres are measured on both faces of each brain slice. The percent infarction is calculated for each brain by the formula: infarct percentage=100×($V_C$−$V_L$/$V_C$), where $V_C$=TTC-stained area in the control hemisphere×slice thickness, $V_L$=TTC-stained area in the infarct hemisphere×slice thickness.[18] Consistent with expert recommendations, the percent brain hemorrhage in the infarct hemisphere is determined by measuring the area of hemorrhage in digital microscopic images on both sides of each brain slice for the ischemic and contralateral, unaffected control hemisphere (in which there is no hemorrhage).[19] The percent hemorrhage=100×(volume of hemorrhage in the infarcted hemisphere/volume of the control hemisphere). The amount of swelling in the ischemic hemisphere is determined by comparing the volume of the ischemic hemisphere and the contralateral hemisphere for both faces of each brain slice. The percent swelling is determined for each brain by the formula: swelling percentage=100×(volume of the infarcted hemisphere−volume of the control hemisphere)/volume of the control hemisphere).

Inclusion and Exclusion Criteria.

All experimental data are included in the analysis with the following exceptions: 1) Experimental failure: The blinded operator notes a technical failure in the anesthesia, surgery, blood sampling, therapy administration, etc.; 2) There is an incorrect placement of the middle artery thromboembolism as noted by a failure of the hemispheric blood flow to decline by at least 80% or pathologic analysis shows that the thrombus is not correctly placed in the proximal MCA; 3) There was a loss of sample for measurement or analyses.

Generation and Characterization of Specific Anti-MMP-9i Monoclonal Antibodies.

MMP-9$^{-/-}$ C57BL/6 mice (Jackson Laboratory, Bar Harbor, Me.) were immunized with recombinant human and mouse MMP-9. Somatic cell fusion of immune splenocytes was performed with SP2/0 cells using conventional hybridoma techniques.[20] Microplate ELISA assays were performed to screen positive clones as described below. Positive clones were subcloned by limiting dilution to create stable monoclonal antibody (mAb) producing hybridomas.

ELISA.

The binding of MMP-9 MAbs to MMP-9 was examined in immune-capture assays. Wells of a microtiter plate were coated with goat anti-mouse IgG whole molecule (Sigma M8642. Lot: 69F-8825), 5 ug/ml. Wells were blocked with 1% BSA for 1 h. After washing, hybridoma culture supernatants or a negative control supernatant were added in duplicate to wells. After 1 h, recombinant anti-His tag human MMP-catalytic subunit was added to the wells for 1 h. After washing, goat anti-His tag-HRP was added (Invitrogen PA120324, 1 mg/ml). After washing, wells were developed with TMB and absorbance at A370 nm was measured. The isotyping of the MAbs was performed by ELISA using a kit as directed (Thermo Fisher Scientific).

Immunoblotting.

The binding of MMP-9i to the full size (~95 kDa) and catalytic subunits (~35 kDa) of human MMP-9. Purified recombinant human MMP-9 (1 ug/lane) were subjected to 7.5% SDS-PAGE under reducing conditions. After electroblotting to PVDF membranes the blots were blocked with 3% BSA and then incubated with purified MMP-9i (1 ug/ml) overnight at 4 deg. C. The blots were washed with TBS-tween and then incubated with a fluorescent antimouse secondary antibody (1:5000, Li-Cor). After washing the blots were developed on a Li-Cor system. The relative migration of standards and the position of MMP-9 proteins are shown.

Purification of mAbs by Affinity Chromatography.

MAbs were purified by affinity chromatography on goat-antimouse agarose columns (goat anti-mouse (H+L) agarose (Invitrogen, Grand Island, N.Y.) as recommended by the manufacturer. Later, there is an additional polishing step (see below) afterward by ion exchange or size exclusion chromatography, dialysis into PBS (pH 7.4) followed by filtration concentration. Endotoxin assays are performed using a limulus lysate assay (ThermoScientific, Waltham, Mass.).

Enzymatic Activity of MMP-9.

Enzymatic activity of MMP-9 was assessed by measuring activity through a coupled assay or by gelatinase activity. To assess gelatinase activity, purified human MMP-9 catalytic domain (2 nM, Neobiolab.com) was mixed with purified monoclonal antibodies to human MMP-9 (120 nM), DQ-gelatin (2.5 ug/ml; Invitrogen) in assay buffer (50 mM Tris HCL, pH 7.6, 150 mM NaCl, 5 mM CaCl2, 0.01% Tween 20) in 96 well black microtiter plates (Costar #3915). The cleavage of DQ-gelatin was monitored by the released fluorescence at 37 degrees C. (ex. 485, em 530 nm). The percent inhibition of MMP-9 activity was determined by comparison to wells without monoclonal antibody. The ability of MMP-9i to inhibit the activity of MMP-9 (1 nM) was assessed in the presence of various amounts of purified MMP-9i (0-128 nM), The IC50 (0.9±0.07 nM) was determined by non-linear regression, $r^2=0.996$. In other experiments, MMP-9 activity was measured in a coupled assay. MMP-9 (4 ng/ml) activity was assessed in the presence of hybridoma supernatants (50 ul) in an MMP-9 assay (GE Healthcare, RPM2634) as described by the manufacturer. The percent inhibition was determined by reference to MMP-9 activity in culture supernatants with MMP-9 (100% activity) and without MMP-9 (control, 0% activity).

Binding avidity was assessed in saturation binding studies of MMP-9i to human MMP-9. Saturation binding of MMP-9i was examined in duplicate in microtiter plate wells coated with human MMP-9 (2 ug/ml), mouse MMP-9 (2 ug/ml), or bovine serum albumin (10 mg/ml). The wells are washed to remove unbound MMP-9 and then non-specific protein binding sites were blocked with 1% bovine serum albumin for 1 hr. After washing, purified MMP-9i antibody diluted in 1% BSA was added to the wells in concentrations from $10^{-8}$ to $10^{-11}$ molar for 1 hr. The wells were washed. Then goat-antimouse Fab peroxidase antibody (1:5000) was added for 1 hr. The wells were washed and TMB (peroxidase substrate) was added to the wells; product formation was monitored continuously at A370. The A370 is plotted vs. concentration of MMP-9i and the data are analyzed with GraphPad Prism to determine the $K_d$. An experiment is considered successful if the data analysis shows a fit with an $r>0.95$.

Statistics.

Data are expressed as means standard error. Differences between two groups were determined by Student's t-test, while a one-way ANOVA with Neuman Keul's correction for multiple statistical inference. A $p<0.05$ was considered to indicate a significant difference. Saturation binding data and inhibitory potency was assessed by nonlinear curve fitting with Graphpad Prism.

Results

Vascular MMP-9 Enhances Ischemic Brain Infarction and Swelling.

Figure 1A:
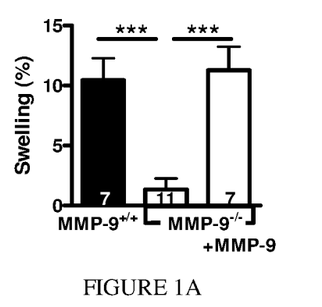
FIGS. 1A-1C show that MMP-9 deficiency markedly reduces brain swelling and infarction after ischemic stroke. After randomization, thromboembolic stroke was performed by a blinded operator in congenic MMP-9$^{+/+}$ (controls) or MMP-9$^{-/-}$ mice given physiologic amounts of MMP-9 (33 ug/kg, Sigma Aldrich) or saline 45 minutes prior to stroke. Brain swelling (FIG. 1A), infarction (FIG. 1B), hemorrhage (FIG. 1C) were measured 24 later in a blinded fashion. Means±SE are shown. The number of animals is indicated. $*p<0.05$, $***p<0.001$ by one-way ANOVA with a Newman Keuls correction for multiple comparison.
Figure 1B:
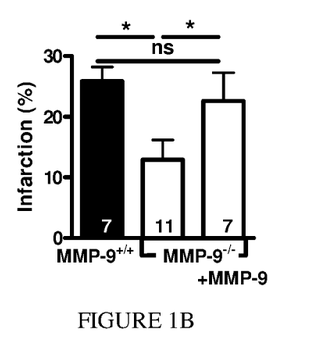
Figure 1C:
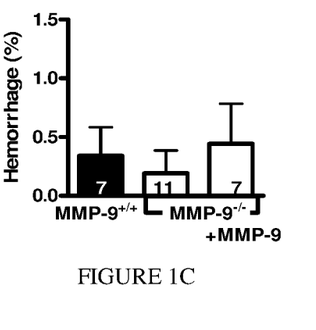

MMP-9 is produced by cells in both the brain and vascular compartments of the neurovascular unit, but the relative contribution of each component to acute ischemic brain injury is debated. By comparison to congenic MMP-9$^{+/+}$ control mice, MMP-9$^{-/-}$ mice showed a marked decreased in brain swelling (FIG. 1A, $p<0.001$). There was significant decrease in brain infarction in MMP-9$^{-/-}$ by comparison to MMP-9$^{+/+}$ mice (FIG. 1B, $p<0.05$). No significant difference was found in brain hemorrhage (FIG. 1C). In these experiments, there were no sex-related differences between MMP-9$^{-/-}$ male and female mice in brain infarction (12.9±3.6% vs. 12.9±7.3%), brain swelling (1.3±1.2% vs. 1.3±1.7%) or brain hemorrhage (0.3±0.3% vs. 0.0±0.0%).

Administration of physiologic amounts of recombinant MMP-9 intravenously to MMP-9-deficient mice significantly increased brain swelling (FIG. 1A, $p<0.001$), restoring it to levels similar to that seen in MMP-9$^{+/+}$ mice. Recombinant MMP-9 also significantly increased brain infarction in MMP-9$^{-/-}$ mice (FIG. 1B, $p<0.05$), returning it to levels comparable to that observed in MMP-9$^{+/+}$ mice. There was a nonsignificant trend to increased hemorrhage in MMP-9$^{-/-}$ mice treated with recombinant MMP-9 (FIG. 1C). These experiments provide evidence that MMP-9 deficiency is protective in acute ischemic stroke and indicate that in the presence of MMP-9 deficiency, vascular MMP-9 alone is sufficient to restore ischemic brain injury to the levels observed in MMP-9$^{+/+}$ mice.

Inhibition of Vascular MMP-9 Reduces Ischemic Brain Injury, Even after Stroke Onset.

Figure 2A:
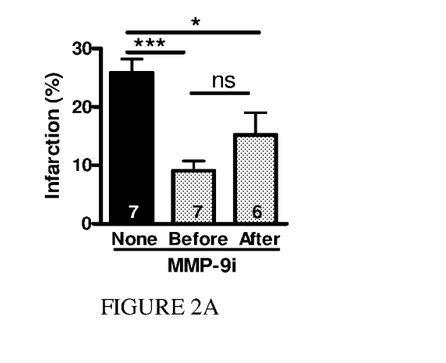
FIGS. 2A-2C show that giving an antibody MMP-9 inhibitor (MMP-9i) before or after stroke onset significantly reduces brain swelling and infarction. Brain infarction (FIG. 2A), swelling (FIG. 2B), and hemorrhage (FIG. 2C) were assessed in congenic MMP-9$^{+/+}$ (wild-type) mice. Mice were administered saline (none, 50 ul) before thromboembolic stroke, an antibody MMP-9i (5 ugs in 50 ul) before thromboembolic stroke, or antibody MMP-9i (5 ugs in 50 ul) 30 minutes after thromboembolic stroke, as indicated. Infarction, swelling, and hemorrhage were measured 24 hours after MCA thromboembolism in a blinded fashion. Experiments were performed in a randomized fashion by an operator blinded to treatment. Means±SE are shown. The number of animals is indicated. $*p<0.05$, $***p<0.001$ by one way ANOVA with a Newman Keuls correction for multiple comparison.
Figure 2B:
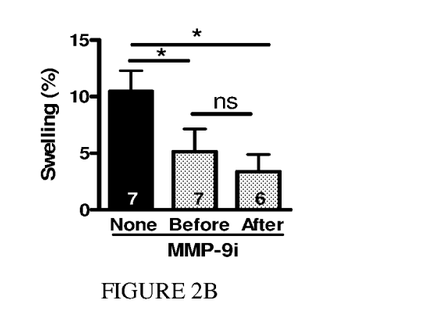
Figure 2C:
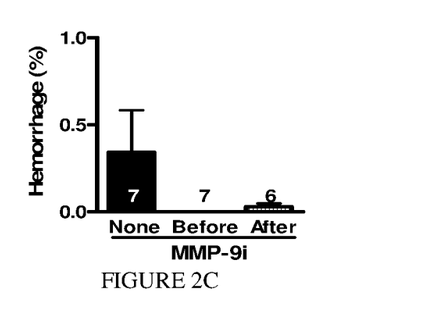

To confirm that vascular MMP-9 specifically contributed to ischemic brain injury in stroke, neutralizing MMP-9-inhibitory (MMP-9i) antibodies were used because antibodies do not cross the blood brain barrier. By comparison to MMP-9$^{+/+}$ (wild-type) mice treated with saline, mice treated with MMP-9i immediately prior to ischemic stroke showed a significant reduction in brain infarction ($p<0.001$) and brain swelling ($p<0.05$) and a trend to a reduction in brain hemorrhage (FIGS. 2A-2C). More importantly, mice treated with an MMP-9i 30 min. after ischemic stroke also showed significant reductions in brain infarction (FIG. 2A, $p<0.05$) and brain swelling (FIG. 2B, $p<0.05$) and there was essentially no brain hemorrhage (FIG. 2C). This is notable because of the short duration of the mouse penumbra and the fact that r-tPA treatment alone, while effective 15 min after stroke, is no longer effective at reducing brain infarction 30 min. after stroke.[14] This indicates that MMP-9i alone has a longer therapeutic time window than r-tPA in an experimental model with translational relevance to human stroke.

Figure 4A:
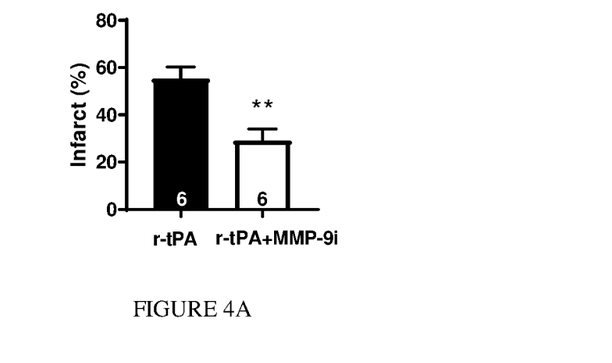
FIGS. 4A-4C show that giving an antibody MMP-9 inhibitor (MMP-9i) with recombinant tissue plasminogen activator (r-tPA) at the time of reperfusion significantly reduces brain infarction (4A), brain hemorrhage (4B) and brain swelling (4C). The middle cerebral artery was occluded by a filament in anesthetized, congenic mice for 180 min. Then mice were treated with r-tPA (10 mgs/kg) with or without an antibody MMP-9i (5 ugs in 100 ul) intravenously, as indicated. The r-tPA was administered 10% as a bolus and 90% over 30 min. Infarction, swelling, and hemorrhage were measured 24 hours in a blinded fashion. Experiments were performed in a by an operator blinded to treatment. Means±SE are shown. The number of animals is indicated. *p<0.05, p<0.01, *p<0.001 by Student's t-test.
Figure 4B:
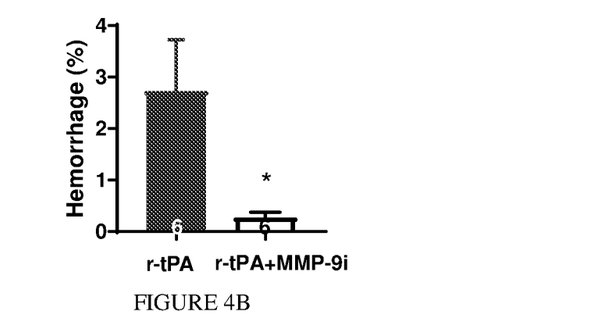
Figure 4C:
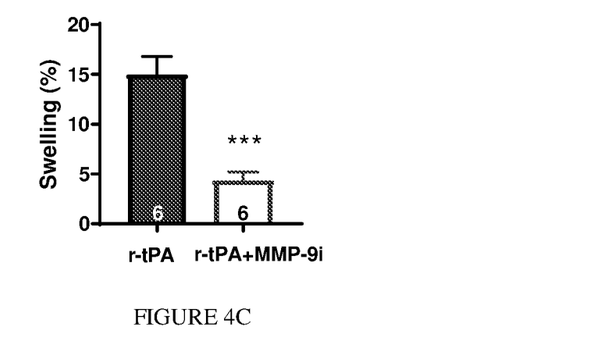

Inhibition of vascular MMP-9 reduces ischemic brain injury after treatment and reperfusion. Recombinant tissue plasminogen activator (r-tPA) is the only approved therapy for ischemic stroke, although other plasminogen activators have shown some efficacy. Ischemia and treatment with r-tPA increase MMP-9 expression. Some patients treated with r-tPA also undergo thrombectomy to remove the vascular thrombotic obstruction. To examine this, we tested whether vascular MMP-9 contributed to ischemic brain injury, hemorrhage and swelling in mice with filament-induced middle cerebral artery occlusion that were treated with r-tPA. Three hours after the onset of ischemia the middle cerebral artery occlusion was removed and mice were treated with r-tPA, with or without MMP-9i. By comparison to mice treated with r-tPA alone, mice treated with r-tPA+MMP-9i showed marked reductions in ischemic infarction (FIG. 4A, $p<0.01$), brain hemorrhage (FIG. 4B, $p<0.05$) and brain swelling (FIG. 4C, $p<0.001$).

MMP-9i Inhibits Human MMP-9 to Reduce Ischemic Brain Injury in a Humanized Model of Experimental Stroke.

Figure 3A:
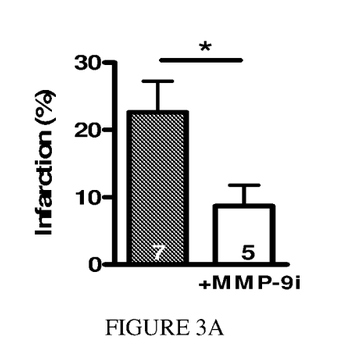
Figure 3B:
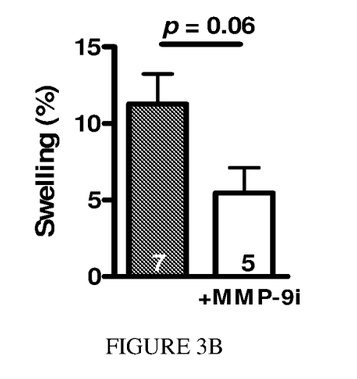

Whether the MMP-9i monoclonal antibody could reduce ischemic brain injury induced by human MMP-9 in a humanized model of ischemic stroke was examined. In this humanized model, MMP-9-deficient (MMP-9$^{-/-}$) mice were administered physiologic amounts of human MMP-9 prior to middle cerebral artery (MCA) thromboembolism. Mice were treated with MMP-9i or saline in a randomized fashion. In MMP-9-deficient mice receiving MMP-9 and saline treatment (placebo), ischemic brain infarction and swelling were not different than that observed in MMP-9$^{+/+}$ mice (compare FIGS. 1A, 1B). However, in MMP-9-deficient mice receiving MMP-9 and MMP-9i treatment, there was ~2.5-fold reduction in brain infarction (FIG. 3A, $p<0.05$), which is comparable to the ~2.2-fold reduction seen in MMP-9$^{-/-}$ mice vs. MMP-9$^{+/+}$ mice (FIG. 1A). The MMP-9i also induced a 2-fold reduction in brain swelling (FIG. 3B, $p=0.06$). There was no significant hemorrhage in either group. These experiments provide additional evidence that a monoclonal MMP-9i is able to engage human MMP-9 in vivo to reduce ischemic brain injury.

Identification of High Avidity, Specific MMP-9 is that Block MMP-9 Activity In Vitro.

Figure 5A:
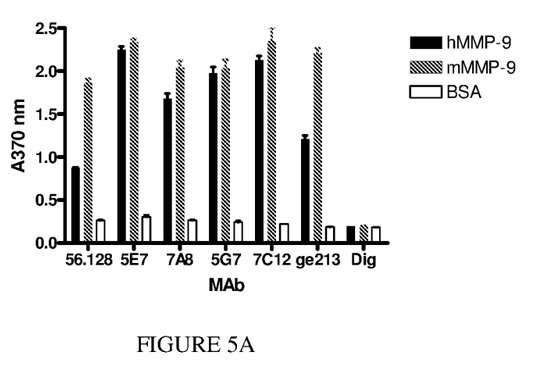
FIG. 5A shows the specific binding of various MMP-9 MAbs, vs. a negative control MAb (Dig), to the recombinant human or mouse catalytic subunit of MMP-9 in a capture immunoassay. Wells of microtiter plates were coated with human or mouse MMP-9 or nothing (2 ug/ml, 25 ul). Wells were washed and blocked with 1% BSA for 1 h. After washing MAbs (2 ug/ml, 25 ul) were added for 1 hr. After additional washing, bound antibody was detected by goat-antimouse peroxidase (1:8000) followed by TMB substrate with detection in a microtiter plate reader at A370 nm.
Figure 5B:
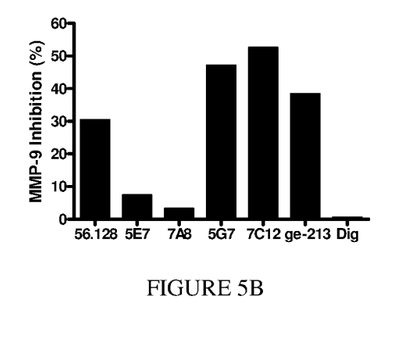
Figure 5C:
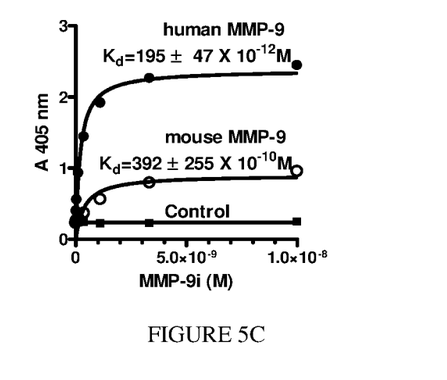
Figure 5D:
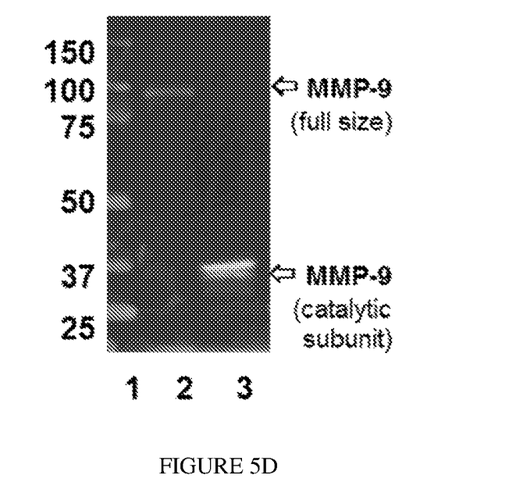

Monoclonal antibodies were produced by somatic cell fusion. Antibodies that bound specifically to the human and/or mouse MMP-9 catalytic subunits were identified in direct or capture immunoassays (FIG. 5A). The ability of different MAbs to inhibit MMP-9 activity was assessed in a gelatinase assay (FIG. 5B). The inhibitory antibodies were of different serotypes: 56.128 (IgG1K), 5E7 (IgG2aK), 7A8 (IgG1K), 5G7 (IgG2aK), 7C12 (IgG1K) and GE-213 (IgG1K). Since these MMP-9i antibodies bound and inhibited the catalytic subunit of MMP-9, one of them (GE-213) was selected as an example to show that inhibition of human MMP-9i reduces brain injury in vivo in experimental ischemic stroke.

Conclusions

The data provides the first evidence that blood (vascular) MMP-9 causes ischemic brain injury and swelling after thromboembolic ischemic stroke. In addition, the data show that treatment of ischemic stroke, by different inhibitory antibodies, markedly reduces ischemic brain injury and swelling. Antibody-mediated inhibition of MMP-9 activity is protective even when given 30 mins after stroke onset. This is notable as in mice with ischemic stroke, treatment with recombinant tissue plasminogen activator, the only proven medical therapy, is no longer effective at reducing ischemic brain injury 30 minutes after stroke onset.[14] In addition to stroke, MMP-9i may also reduce tissue injury in other organs were MMP-9 activity is induced by ischemia, such as the liver, limbs or heart.

REFERENCES

1. Van den Steen P E, Dubois B, Nelissen I, Rudd P M, Dwek R A, Opdenakker G. Biochemistry and molecular biology of gelatinase B or matrix metalloproteinase-9 (MMP-9). *Crit Rev Biochem Mol Biol.* 2002; 37:375-536
2. Yabluchanskiy A, Ma Y, Iyer R P, Hall M E, Lindsey M L. Matrix metalloproteinase-9: Many shades of function in cardiovascular disease. *Physiology* (Bethesda). 2013; 28:391-403
3. Hamada T, Fondevila C, Busuttil R W, Coito A J. Metalloproteinase-9 deficiency protects against hepatic ischemia/reperfusion injury. *Hepatology.* 2008; 47:186-198
4. Fujimura M, Gasche Y, Morita-Fujimura Y, Massengale J, Kawase M, Chan P H. Early appearance of activated matrix metalloproteinase-9 and blood-brain barrier disruption in mice after focal cerebral ischemia and reperfusion. *Brain Res.* 1999; 842:92-100
5. Rosell A, Cuadrado E, Ortega-Aznar A, Hernandez-Guillamon M, Lo E H, Montaner J. MMP-9-positive neutrophil infiltration is associated to blood-brain barrier breakdown and basal lamina type IV collagen degradation during hemorrhagic transformation after human ischemic stroke. *Stroke.* 2008; 39:1121-1126
6. Zhao B Q, Wang S, Kim H Y, Storrie H, Rosen B R, Mooney D J, Wang X, Lo E H. Role of matrix metalloproteinases in delayed cortical responses after stroke. *Nat Med.* 2006; 12:441-445
7. Chaturvedi M, Kaczmarek L. Mmp-9 inhibition: a therapeutic strategy in ischemic stroke. *Mol Neurobiol.* 2014; 49:563-573
8. Asahi M, Wang X, Mori T, Sumii T, Jung J C, Moskowitz M A, Fini M E, Lo E H. Effects of matrix metalloproteinase-9 gene knock-out on the proteolysis of blood-brain barrier and white matter components after cerebral ischemia. *J Neurosci.* 2001; 21:7724-7732
9. Harris A K, Ergul A, Kozak A, Machado L S, Johnson M H, Fagan S C. Effect of neutrophil depletion on gelatinase expression, edema formation and hemorrhagic transformation after focal ischemic stroke. *BMC Neurosci.* 2005; 6:49
10. Copin J C, Bengualid D J, Da Silva R F, Kargiotis O, Schaller K, Gasche Y. Recombinant tissue plasminogen activator induces blood-brain barrier breakdown by a matrix metalloproteinase-9-independent pathway after transient focal cerebral ischemia in mouse. *Eur J Neurosci.* 2011; 34:1085-1092
11. Suzuki Y, Nagai N, Umemura K, Collen D, Lijnen H R. Stromelysin-1 (MMP-3) is critical for intracranial bleeding after t-PA treatment of stroke in mice. *J Thromb Haemost.* 2007; 5:1732-1739
12. Aoki T, Sumii T, Mori T, Wang X, Lo E H. Blood-brain barrier disruption and matrix metalloproteinase-9 expression during reperfusion injury: mechanical versus embolic focal ischemia in spontaneously hypertensive rats. *Stroke*. 2002; 33:2711-2717
13. Gidday J M, Gasche Y G, Copin J C, Shah A R, Perez R S, Shapiro S D, Chan P H, Park T S. Leukocyte-derived matrix metalloproteinase-9 mediates blood-brain barrier breakdown and is proinflammatory after transient focal cerebral ischemia. *Am J Physiol Heart Circ Physiol*. 2005; 289:H558-568
14. Reed G L, Houng A K, Wang D. Microvascular Thrombosis, Fibrinolysis, Ischemic Injury, and Death After Cerebral Thromboembolism Are Affected by Levels of Circulating alpha2-Antiplasmin. *Arterioscler Thromb Vasc Biol*. 2014; 34:2586-2593
15. Houng A K, Wang D, Reed G L. Reversing the deleterious effects of alpha2-antiplasmin on tissue plasminogen activator therapy improves outcomes in experimental ischemic stroke. *Exp Neurol*. 2014; 255C:56-62
16. Saleem S, Li R C, Wei G, Dore S. Effects of EP1 receptor on cerebral blood flow in the middle cerebral artery occlusion model of stroke in mice. *J Neurosci Res*. 2007; 85:2433-2440
17. King S M, McNamee R A, Houng A K, Patel R, Brands M, Reed G L. Platelet dense-granule secretion plays a critical role in thrombosis and subsequent vascular remodeling in atherosclerotic mice. Circulation. 2009; 120:785-791
18. Swanson R A, Morton M T, Tsao-Wu G, Savalos R A, Davidson C, Sharp F R. A semiautomated method for measuring brain infarct volume. *J Cereb Blood Flow Metab*. 1990; 10:290-293
19. Fagan S C, Lapchak P A, Liebeskind D S, Ishrat T, Ergul A. Recommendations for preclinical research in hemorrhagic transformation. *Transl Stroke Res*. 2013; 4:322-327
20. Nelson P N, Reynolds G M, Waldron E E, Ward E, Giannopoulos K, Murray P G. Monoclonal antibodies. *Mol Pathol*. 2000; 53:111-117

The invention claimed is:

1. A method of treating tissue injury after the onset of ischemia induced by thromboembolism comprising:
   determining that a subject will be or is in need of therapy to reduce ischemic injury; and
   administering intravenously to the subject a therapeutically effective amount of a vascular-selective matrix metalloproteinase 9 (MMP-9) inhibitor that does not cross the intact blood-brain barrier to treat tissue injury after the onset of ischemia, wherein the MMP-9 inhibitor is an antibody or fragment thereof that binds MMP-9.

2. The method of claim 1, wherein the subject is a human.

3. The method of claim 2, wherein the vascular-selective MMP-9 inhibitor is a monoclonal antibody or fragment thereof that binds human MMP-9.

4. The method of claim 1, wherein the vascular-selective MMP-9 inhibitor is administered at least fifteen minutes after thromboembolic stroke in the subject.

5. The method of claim 4, wherein the vascular-selective MMP-9 inhibitor is administered at least thirty minutes after thromboembolic stroke in the subject.

6. The method of claim 1, wherein the subject is further treated with tissue plasminogen activator or other therapy before or after the administration of the vascular-selective MMP-9 inhibitor.

7. The method of claim 1, wherein the subject is treated with a stentreiever or other type of thrombectomy device before or after the administration of the vascular-selective MMP-9 inhibitor.

8. The method of claim 1, wherein administration of the vascular-selective MMP-9 inhibitor decreases vascular MMP-9 activity in the subject.

9. The method of claim 1, wherein administration of the vascular-selective MMP-9 inhibitor decreases, ischemic cell death, organ swelling, organ hemorrhage, blood barrier breakdown, fibrin deposition, or a combination thereof.

10. The method of claim 1, wherein administration of the vascular-selective MMP-9 inhibitor decreases cerebral infarction, ischemic cell death, brain swelling, brain hemorrhage, blood-brain barrier breakdown, fibrin deposition, or a combination thereof.

11. The method of claim 1, wherein the vascular-selective MMP-9 inhibitor specifically binds a catalytic subunit of MMP-9.

12. The method of claim 1, wherein the subject has ischemic injury to a tissue selected from a brain, a liver, a limb, a heart, or a combination thereof.

13. A method of treating ischemic stroke induced by thromboembolism comprising administering intravenously to a human subject in need thereof a treatment effective amount of vascular-selective MMP-9 inhibitor that does not cross the blood-brain barrier and a plasminogen activator, wherein the MMP-9 inhibitor is an antibody or fragment thereof that binds MMP-9.

14. The method of claim 13, wherein the vascular-selective MMP-9 inhibitor is a monoclonal antibody or fragment thereof that binds human MMP-9 and the plasminogen activator is tissue plasminogen activator (tPA).

* * * * *